United States Patent [19]
Howarth

[11] Patent Number: 5,403,300
[45] Date of Patent: Apr. 4, 1995

[54] TAMPONS

[75] Inventor: George Howarth, Solihull, United Kingdom

[73] Assignee: Smith & Nephew p.l.c., United Kingdom

[21] Appl. No.: 227,561

[22] Filed: Apr. 14, 1994

Related U.S. Application Data

[63] Continuation of Ser. No. 24,822, Mar. 1, 1993, abandoned, which is a continuation of Ser. No. 730,978, Jul. 29, 1991, abandoned.

Foreign Application Priority Data

Mar. 31, 1989 [GB] United Kingdom ............... 8907302

[51] Int. Cl.$^6$ ........................ A61F 13/15; A61F 13/20
[52] U.S. Cl. ........................ 604/384; 604/358; 604/366; 604/370; 604/385.1; 604/904
[58] Field of Search ............... 604/358, 366, 369, 363, 604/370, 371, 372, 378, 380, 384, 385.1, 904; 602/58-59

[56] References Cited

U.S. PATENT DOCUMENTS

| | | | |
|---|---|---|---|
| 2,771,882 | 11/1956 | Leupold | 604/385.1 |
| 2,902,038 | 9/1959 | Bletzinger et al. | 604/384 |
| 2,986,780 | 6/1961 | Bletzinger | 604/385.1 |
| 3,053,252 | 9/1962 | Wolf | 604/385.1 |
| 3,986,511 | 10/1976 | Olofsson et al. | 604/385.1 |
| 3,994,298 | 11/1976 | Des Marais | 604/385.1 |
| 4,027,673 | 6/1977 | Poncy et al. | 604/385.1 |
| 4,175,561 | 11/1979 | Hirschmann | 604/385.1 |
| 4,211,225 | 7/1980 | Sibalis | 604/385.1 |
| 4,351,339 | 9/1982 | Sneider | 604/385.1 |
| 5,318,552 | 6/1994 | Shiba et al. | 604/372 |

FOREIGN PATENT DOCUMENTS

| | | |
|---|---|---|
| 0215417 | 3/1987 | European Pat. Off. |
| 1334788 | 10/1973 | United Kingdom |
| 8403833 | 10/1984 | WIPO |
| 8905621 | 6/1989 | WIPO |

*Primary Examiner*—Randall L. Green
*Assistant Examiner*—P. Zuttarelli
*Attorney, Agent, or Firm*—Rosenman & Colin

[57] ABSTRACT

A tampon for hygienic use comprising a generally cylindrical absorbent core having a liquid pervious cover layer on the outer surface thereof wherein the cover layer is a polymer net comprising two intersecting sets of parallel ribs and wherein each set of ribs are aligned obliquely with respect to both the main axis of the tampon and to each other. A strip of net may be bonded to one end of a strip of absorbent material and the composite spirally wound such that the net forms the outer layer. The free end of the net may overlap an underlying layer of net and be bonded thereto by heat sealing.

18 Claims, 1 Drawing Sheet

TAMPONS

This application is a continuation of U.S. application Ser. No. 08/024,822, filed 1 Mar. 1993, now abandoned, which is a continuation of U.S. application Ser. No. 07/730,978 filed 29 Jul. 1991, now abandoned.

FIELD OF THE INVENTION

The present invention relates to tampons for hygienic use and to processes for their preparation.

BACKGROUND OF THE INVENTION

Conventional tampons for hygienic use normally comprise an absorbent core containing hydrophilic material such as hydrophilic foam or fibres which has been formed into general cylindrical shape by for example compressing or moulding. Conventional tampons, however, have been found to be relatively uncomfortable to insert into the vagina due to the "dry feel" and abrasiveness of the absorbent fibre or foam surface of the absorbent core of these tampons. Furthermore conventional tampons which comprise an absorbent core containing hydrophilic cellulose fibres such as wood pulp fibres tend to shed these fibres when the absorbent core becomes moist in use, and in particular during insertion or removal of the tampon from the vagina. It is known from the disclosure of European Patent No. 149155 and United Kingdom Patent Nos. 1218641 and 2010680 that the absorbent core of tampons of this type can be provided with a liquid pervious non-woven fabric cover layer to inhibit in use shedding of fibres from the absorbent core. It is further disclosed in the aforementioned European Patent No. 159155 that such a non-woven fabric cover layer can also render the tampon more comfortable to insert into the vagina because the smoother nature of the non-woven fabric reduces the surface drag or resistance of the tampon during insertion. It has now been found that similar advantages can be obtained using an alternative cover layer material over the absorbent core of a tampon.

SUMMARY OF INVENTION

We have now found that a tampon for hygienic use which comprises a generally cylindrical absorbent core having a liquid pervious cover layer on the outer surface thereof can be provided for comfortable insertion into the vagina wherein the cover layer is a net of plastics material comprising two intersecting sets of parallel ribs and wherein each set of ribs lie in a direction which is oblique both to the main axis of the tampon and to each other.

Accordingly the present invention provides a tampon for hygienic use comprising a generally cylindrical absorbent core having a liquid pervious cover layer on the outer surface thereof wherein the cover layer is a polymer net comprising two intersecting sets of parallel ribs and wherein each set of ribs are aligned obliquely with respect to both the main axis of the tampon and to each other.

The net cover layer of the tampon of the invention however does not have ribs which lie in a direction substantially perpendicular or normal to the main axis of the tampon. Such perpendicular direction ribs tend to give the net cover layer a "rough feel" during insertion of the tampon into the vagina.

The intersecting ribs of the net cover layer of the tampon of the invention can have several different arrangements.

Suitable arrangements include those in which one set of ribs lie in a direction which is parallel to the main axis of the tampon.

DETAILED DESCRIPTION OF THE INVENTION

Figure 1:
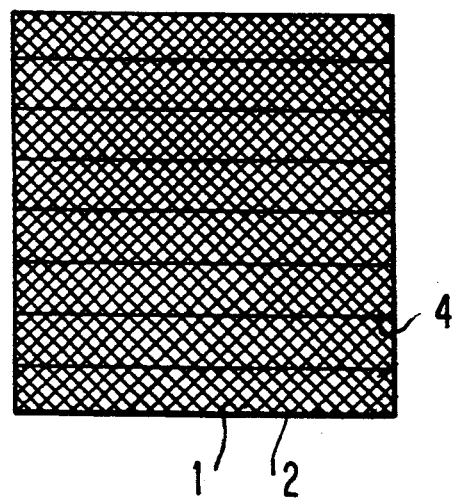
FIG. 1 shows a plan view of the net on the tampon of the present invention.
Figure 2:
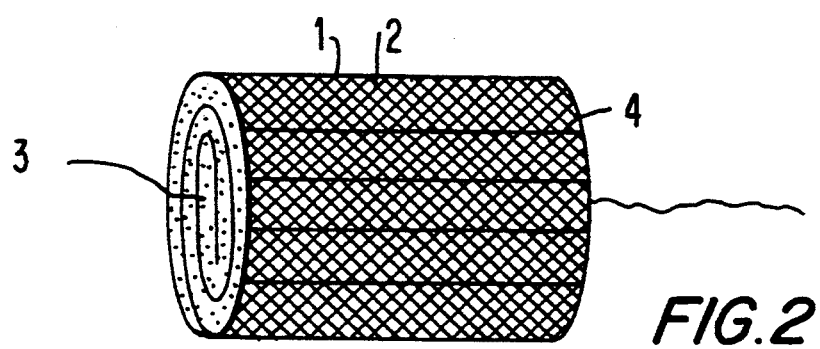
FIGS. 2 and 3 show the orientation of the net on the tampon of the present invention. The two intersecting sets of parallel ribs 1, 2 are aligned obliquely with respect to both the main axis 3 of the tampon and to each other and with a further set of parallel ribs 4 aligned parallel to the main axis of the tampon.
Figure 3:
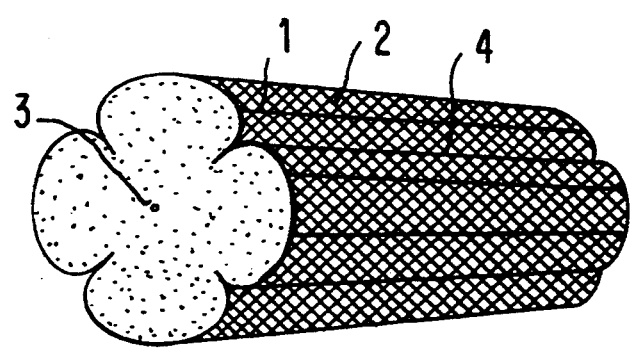

Thus in an embodiment of the invention in which the net cover layer comprises three sets of parallel ribs, one of the sets can be in a direction parallel to the main axis of the tampon and the other two sets can be in a direction which is oblique to the main axis and to each other.

However, in favoured embodiments of the invention, the net cover layer comprises two sets of parallel ribs both of layer which lie in a direction which is oblique to the main axis of the tampon and to each other.

In such favoured embodiments it is preferred that the two sets of ribs lie in intersecting directions which are inclined at substantially the same angle to the main axis of the tampon.

In such embodiments therefore the angle of inclination of each set of ribs to the main axis of the tampon will be about half the angle of intersection of the two sets of ribs.

The net cover layer used in the invention will preferably have a uniform pattern of two intersecting sets of ribs. In preferred embodiments of the invention the net cover layer has diamond pattern of two intersecting set of ribs in which the sets of ribs intersect at an angle of 60° to 120° for example 90° and which are aligned at about 30° to 60° for example 45° to the main axis of the tampon. Tampons with such net cover layers have been found easy and comfortable to insert into the vagina without trauma.

The ribs of the two intersecting sets can have a different thicknesses. The ratio of thickness of one set of ribs to the other set of ribs however is desirably not greater than 2:1 and preferably not greater than 3:2 for example a ratio of 1:1 that is sets of ribs of approximately equal thickness to prevent the net having a rough feel.

The net used in the invention has holes or apertures which to some extent are defined by the intersecting sets of ribs.

The net can suitably have 4 to 20 ribs/cm and can preferably have 5 to 15 ribs/cm.

It has been found that densities of ribs within the hereinabove ranges can provide a plastics material with holes which are sufficiently small to inhibit penetration of the material by moist fibres. Such a plastics material when used as a cover layer over the absorbent core of a tampon of the invention will therefore advantageously inhibit shedding of fibres from the absorbent core during use.

Favourably the area of each aperture may be from 0.01 sq. mm to 1 sq. mm and more favourably 0.1 sq. mm to 1 sq. mm and preferably 0.2 to 0.9 sq. mmm for example 0.5 to 0.7 sq. mm. Suitably the apertures can have a diamond, circular or like shape.

Suitably the open area of the net may comprise from 5% to 70% of the area of the film and more suitably 20% to 60% of the area of the film for example 30% to 50%.

Aptly the net for use in the invention can have a weight per unit area of upto 50 g/m² suitably from 10 to 50 g/m², desirably from 15 to 45 g/m² and preferably of from 20 to 40 g/m² for example 25 to 35 g/m².

Aptly the net for use in the invention can have a thickness of upto about 0.25 mm suitably 0.03 mm to 0.15 mm and preferably have a thickness of 0.04 mm to 0.12 mm for example 0.06 mm to 0.11 mm.

Plastics materials of the net used in the invention will normally comprise a polymer which is relatively non-water absorbent to provide the tampon of the invention with a cover layer which is similarly non-water absorbent. The polymer is preferably a thermoplastic to render the plastics material advantageously heat sealable.

The plastics materials can advantageously also comprise an elastomeric polymer to render the net cover layer comfortable and provide it with a soft "feel".

Suitable elastomeric polymers include polyether ester, polyurethanes, styrene-butadiene and styrene-isoprene block copolymers, polyisobutadiene and ethylene-vinyl acetate copolymers.

Favoured elastomeric polymers are thermoplastic polymers. Suitable thermoplastic elastomeric polymers include ethylene-vinyl acetate copolymers and polyether ester and polyether amide block copolymers.

Apt ethylene vinyl acetate copolymers for use in the invention are known as Evatane (Trade Mark) such as Evatane 1020.

Apt polyether ester block copolymers for use in the invention are known as Hytrel (Trade Mark) such as Hytrel 4056.

Apt polyether amide block copolymers are known as Pebax (Trade Mark) such as Pebax 2533 SN 00.

Plastics materials which are suitable for preparing the nets used in the invention include thermoplastic elastomeric polymers or blends of these polymers with other polymers. Favoured polymeric materials comprise a blend of an elastomeric polymer such as ethylene-vinyl acetate copolymer and one or more incompatible polymers such as a polyolefin other suitable blends include those of polyurethane or polyisobutadiene with an incompatible polymer such as polyolefin.

An "incompatible polymer" is a polymer which in a blend therewith is not miscible with the elastomeric polymer. In such a blend the polymers would form separate phases and the polymer in the lower concentration would form a discrete disperse phase and the polymer present in the higher concentration would form a continuous phase.

Suitable incompatible polymers include polyolefins such as polystyrene for example rubber modified polystyrene (High impact polystyrene), polypropylene and high density and linear low density (LLD) polyethylene.

Apt polymer containing ethylene-vinyl acetate copolymers blends for use in the invention include those described in EP 0141572.

Suitable blends for use in the invention can comprise 10 to 95% by weight of the elastomeric polymer, desirably 15% to 90% by weight and can preferably comprise 20% to 85% by weight of the elastomeric polymer. Such blends may include up to 10% by weight of filler or whitening agents such as titanium dioxide, and of 3% by weight of an additive such as surfactant. A favoured polymeric material comprises a blend of 15% to 35% by weight ethylene vinyl acetate copolymer, 60% to 80% by weight of a mixture of linear low density polyethylene and high impact polystyrene and 0 to 10% by weight of titanium dioxide.

An apt plastics material of this type comprises a blend of 24% to 27% by weight of ethylene vinyl acetate, 55% to 65% by weight of linear low density polyethylene, 10% to 15% by weight of high impact polystyrene and 2% to 5% by weight of titanium dioxide. An apt net of this plastics materials for use in the invention is known as Net 909 (Trade Mark) reference LE6 H30 available from Smith & Nephew Plastics Ltd.

Other polymer blends for use in the invention include blends comprising polyurethane or polybutadiene. Such materials are described in EP 046071 and EP 072258.

Such a net has a diamond pattern of two sets of intersecting ribs (approximately 7 ribs/cm in each direction), a weight per unit area of 30±4 g/m² and an open area of approximately 40%.

Another favoured polymeric material comprises a blend of 36% to 50% by weight of ethylene vinyl acetate copolymer, 45% to 60% by weight of a mixture of linear low density polyethylene and high impact polystyrene and 0% to 10% by weight of titanium dioxide.

An apt polymeric material of this type is a polymer blend containing 36% to 40% by weight of ethylene vinyl acetate, 36% to 40% by weight of linear low density polyethylene, 17% to 21% by weight of high impact polystyrene up to 5% by weight of titanium dioxide and up to 2% by weight of an antistatic agent.

The net for use in the invention, however, can advantageously comprise a composite material which comprises a substrate layer of higher melting point polymer and a heat sealable layer of a lower melting point polymer. Suitable plastics material of this type are given in United Kingdom Patent No. 2142246.

Nets for use in the invention can be made by any suitable thermoforming method from a plastics material. Typical nets are integral nets that is nets in which the ribs and junctures are formed integrally. Such nets can be made by extruding the plastics material through holes or cavities of contra-rotating or reciprocating dies. Alternatively the nets can be made by cast extruding the plastics material as a ribbed embossed film using grooved embossing rollers of a suitable pattern and forming holes or apertured in the embossed film by stretching or perforating the film by conventional means or a combination of these methods.

Suitable methods of forming nets by embossing for use in the invention are given in United Kingdom Patent No. 1110051 and European Patent No. 0141592.

The absorbent core of the tampon of the invention will normally comprise a hydrophilic material such as hydrophilic fibres or hydrophilic foam. Suitable hydrophilic fibres include conventional hydrophilic cellulosic fibres such as wood pulp viscose or cotton fibres. A minor amount of hydrophobic fibres however may be present in the absorbent core.

The absorbent core of the tampon will preferably comprise compressed hydrophilic fibres to render the tampon expandable during use. Favoured tampons of this type expand in a lateral direction in use. Preferred lateral expanding tampons comprise a radially compressed spirally wound strip of hydrophilic fibres. Tampons of this type are disclosed in aforementioned European Patent No. 149155.

The net cover layer can cover the whole of the surface of the absorbent core of tampon. It is preferred however that the net cover layer covers only the side or generally cylindrical surface of the absorbent core.

The net cover layer can advantageously be attached to the surface of the absorbent core to inhibit displacement of the layer during insertion or withdrawal of the tampon. The net cover layer can be attached to the surface of the absorbent core by means of a conventional bonding method such as adhesive bonding or preferably heat bonding. The net for example in the form of a strip may be heat bonded to the surface of the absorbent core over the whole or preferably over a part of its area of length. The bonded area may be continuous or discontinuous portion for example in the form of strips or dots.

The tampon of the invention can optionally be provided with a rounded insertion end to facilitate insertion of the tampon into the vagina.

The tampon can be packaged in a conventional over wrap for use as a digital tampon or within an applicator package for insertion by means of an applicator.

In another aspect of the present invention a tampon may be formed by a process which comprises spirally winding a strip of absorbent material which is attached at an end portion thereof to a strip of liquid pervious material and radially compressing the wound strip to form a tampon which comprises an absorbent core of general cylindrical shape having a cover layer of the liquid pervious material on the outer surface thereof wherein the cover layer net is a plastics material comprising two intersecting sets of ribs and wherein each set of ribs lie in a direction which is oblique to the main axis of the tampon and to each other.

In accordance with this embodiment of the invention there is provided a tampon comprising a strip of absorbent material having a strip of liquid pervius polymer net attached at one end being spirally wound to form a generally cylindrical absorbent core having an outer cover layer of polymer net, wherein the net comprises two intersecting sets of parallel ribs, each of said sets being obliquely aligned with respect to each other and to the major axis of the cylindrical core.

The net covered tampon core may radially compressed to form a tampon whose cylindrical surface is comprised of a number of convoluted folds extending longitudinally parallel to the main axis of the tampon the covered core can be radially compressed by a conventional method such as the methods disclosed in European Patent No. 149155 and United Kingdom No. 1082440 to form a tampon of the invention.

The strip of liquid pervious net will normally have a length similar to that of the length of the formed tampon. The length of the strip of liquid pervious net may be greater than the width of the strip of absorbent material to ensure that the liquid pervious material covers one or both ends of the wound strip.

It is preferred however that the length of the strip of liquid pervious net is the same or less than the width of the strip of absorbent material to ensure that the liquid pervious material covers only the cylindrical side surfaces of the core.

At least two sets of the parallel ribs in the strip of liquid pervious material will normally lie in obliquely to the transverse axis of the strip to ensure that these two sets of parallel ribs of the liquid pervious net cover layer on the tampon will lie obliquely to the longitudinal or main axis direction of the tampon when formed.

The strip of liquid pervious material can be attached to the strip of absorbent material by any convenient bonding method such as adhesive or heat bonding. It is preferred that a heat bonding method is used. Suitable bonding methods include those given aforementioned European Patent No. 149155.

The strip of liquid pervious material will be attached to the end portion of the strip of absorbent material.

The combined strip can be spirally wound by a conventional method such as the methods disclosed in European Patent No. 149155 and United Kingdom Patent No. 1392995.

The strip of liquid pervious material will aptly have a width which is sufficient to cover the wound strip and is suitably long enough to extend around the circumference of the core. Preferably the width of the liquid pervious material is sufficient to overlap the attached portion of the net.

The unattached free end portion of the liquid pervious material which overlaps the attached portion thereof and can be then bonded to the underlying portion of the cover layer by a suitable method for example heat bonding to secure the wound strip. The free end of the net may also be sealed to the core material.

The unattached end portion may be bonded to the overlying layer of net over an distance of at least 10% of the circumference of its core and preferably, upto 90% of its circumference. The free end of the net may be bonded to the underlying portion thereof over a distance or length corresponding to the length of the core.

The tampon may be provided with a rounded end by conventional method such as the method disclosed in United Kingdom Patent No. 1046066.

EXAMPLE

A strip of liquid pervious net plastics material (length 110 m width 48 mm) was attached at a overlap end portion (length 30 mm) by heat sealing the one end of a strip (width 52 mm length 250 mm) of viscose fibres and the combined strip spirally wound to form an absorbent core of general cylindrical shape having a cover layer of the plastics material over its side surface. The non-attached end portion (length 16 mm) of the plastics material was then heat sealed over the attached end portion to hold the cover layer in place. The core cover layer was then radially compressed to form a tampon of the invention (diameter 14–17 mm).

The plastics material used in this Example (known as net 909 ref LE6 H30) had two sets of intersecting parallel straight ribs (approximately 7/cm) and a weight per unit area of $30\pm4$ g/m$^2$. The two sets of ribs of the net cover layer had intersecting directions which were inclined at the same angle (30°–45°) to the longitudinal axis of the tampon. The strip was spirally wound by the method given in United Kingdom Patent No. 1392995 and the wound strip radially compressed by the method given in United Kingdom No. 082770.

In a subjective test, it was found that tampons of the invention were significantly better with respect to ease of insertion and withdrawal at both the beginning and end of menstruation than tampons of similar construction but not provided with a cover layer.

I claim:

1. A tampon for hygienic use comprising a generally cylindrical absorbent core having a central longitudinal axis and an outer surface with a liquid pervious cover layer thereon wherein the cover layer is a polymer net comprising two intersecting sets of parallel ribs and wherein each set of ribs are aligned obliquely with respect to the central longitudinal axis of the tampon and to each other, and also comprising a set of parallel ribs aligned parallel to the central longitudinal axis of the tampon and excluding ribs which lie in a direction perpendicular to the central longitudinal axis of the tampon.

2. A tampon according to claim 1 wherein each set of ribs are of equal thickness.

3. A tampon according to claim 1 wherein each set of obliquely aligned ribs are aligned at an angle of from 30° to 60° with respect to the central longitudinal axis of the tampon.

4. A tampon according to claim 1 wherein the aligned ribs are aligned at an angle of from 60° to 120° with respect to each other.

5. A tampon according to claim 1 wherein the net contains from 4 to 20 ribs/cm.

6. A tampon according to claim 1 wherein the polymer comprises a thermoplastic polymer.

7. A tampon according to claim 1 wherein the polymer comprises an elastomer.

8. A tampon according to claim 1 wherein the polymer comprises a blend of an ethylene-vinyl acetate copolymer, a linear low density polyethylene and a high impact polystyrene.

9. A tampon according to claim 1 wherein core and cover layer are radially compressed.

10. A tampon according to claim 1 wherein the polymer comprises a blend of an elastomer and an incompatible polymer.

11. A tampon according to claim 10 wherein the incompatible polymer is a polyolefine.

12. A tampon as claimed in claim 1 wherein the net comprises a composite material comprising two layers one of which is of a polymer having a melting point which is lower than that of the polymer forming the other layer.

13. A tampon according to claim 12 wherein the free end of the cover layer overlaps the other end of the cover layer and is sealed to an underlying portion of the cover layer.

14. A tampon according to claim 12 wherein the free end of the cover layer is sealed to the absorbent core.

15. A tampon according to claim 12 wherein the free end of the cover layer is heat sealed.

16. A tampon comprising a strip of absorbent material having a strip of liquid pervious polymer not attached to one end and being spirally wound to form a generally cylindrical absorbent core having an outer cover layer of polymer net, wherein the net comprises two intersecting sets of parallel ribs, each of said sets being obliquely aligned with respect to each other and to the central longitudinal axis of the cylindrical core, and a set of parallel ribs aligned parallel to the main axis of the tampon and wherein the net excludes ribs which lie in a direction perpendicular to the central longitudinal axis of the tampon.

17. A tampon according to claim 16 wherein the length of the cover layer is not less than that of the circumference of the core.

18. A tampon according to claim 17 wherein the free end of the cover layer is sealed over the length of the absorbent core.

* * * * *